(12) United States Patent
Ghosh et al.

(10) Patent No.: US 6,221,374 B1
(45) Date of Patent: Apr. 24, 2001

(54) CONTROLLED RELEASE COMPOSITIONS

(75) Inventors: Tirthankar Ghosh, Oreland; Edwin H. Nungesser, Horsham, both of PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/073,282

(22) Filed: May 6, 1998

Related U.S. Application Data
(60) Provisional application No. 60/047,966, filed on May 28, 1997.

(51) Int. Cl.$^7$ .................................................. A01N 25/02
(52) U.S. Cl. ...................... 424/405; 424/406; 424/407; 424/411; 514/372; 514/731; 514/734
(58) Field of Search .................................. 514/360, 372, 514/731–737; 424/404–407, 409, 411–413

(56) References Cited

U.S. PATENT DOCUMENTS

| | | | | |
|---|---|---|---|---|
| 4,129,448 | * | 12/1978 | Greenfield et al. ................. | 106/18.32 |
| 5,364,977 | | 11/1994 | Asai et al. ............................ | 568/720 |

FOREIGN PATENT DOCUMENTS

| | | |
|---|---|---|
| 2015497 | 10/1971 | (DE) . |
| 4140928A1 | 6/1993 | (DE) . |
| 709 358 A1 | 5/1996 | (EP) . |
| 52-038005 | 3/1977 | (JP) . |
| 52-38005 | 3/1977 | (JP) . |
| 63-111004 | 5/1988 | (JP) . |
| 4-202263 | 7/1992 | (JP) . |
| 6-166733 | 6/1994 | (JP) . |
| 07 003 191 | 1/1995 | (JP) . |
| 7-69809 | 3/1995 | (JP) . |
| 069960B | 4/1982 | (RO) . |

OTHER PUBLICATIONS

American Wood Preservers Association Standard M11–87, "Standard Method of Determining the Leachability of Wood Preservatives" 1987.

European Search Report dated Sept. 30, 1998; Application No. EP 98 30 3785.

* cited by examiner

*Primary Examiner*—Neil S. Levy
(74) *Attorney, Agent, or Firm*—S. Matthew Cairns; Kenneth Crimaldi

(57) ABSTRACT

Disclosed are compositions containing biologically active compounds that slowly release the biologically active compound. These compositions may be directly incorporated into the locus to be protected or may be applied to a structure in a coating.

14 Claims, No Drawings

CONTROLLED RELEASE COMPOSITIONS

This is a nonprovisional application of prior pending provisional application Ser. No. 60/047,966 filed May 28, 1997.

BACKGROUND OF THE INVENTION

This invention relates generally to a composition for controlling the release of biologically active compounds. In particular, this invention relates to the use of certain polyphenolic compounds to control the release of biologically active compounds.

The ability to control release of biologically active compounds to a locus to be protected is important in the field of biologically active compounds. Typically, when a biologically active compound is added to a locus to be protected, the compound is rapidly released, whether or not it is needed. Controlled release compositions deliver the biologically active compound in a manner that more closely matches the need for the compound. In this way, only the amount of the biologically active compound needed is released into the locus to be protected. Controlled release offers the advantages of reduced cost, lowered toxicity and increased efficiency.

Various methods of controlled release are known. Such methods include encapsulation of the biologically active compound, adsorption of the biologically active compound on an inert carrier, such as silica gel, and clathration of the biologically active compound.

All of these methods have drawbacks to widespread commercial use, such as expensive starting materials, limited compatibility of the controlled release method to the compounds to be released or locus to be protected, and limited control of the release of the biologically active compounds. For example, whether a clathrate forms is solvent dependent, which limits available solvent choices. An additional problem with clathrates is that solvent, rather than the desired biologically active compound, is sometimes incorporated into the complex.

For example, EP 709 358 A (Suzuki et al.) discloses a clathrate of isothiazolones using a tetrakisphenol compound. Although these compositions provide some control of the release of the isothiazolone, the amount of control is limited and the tetrakisphenol compound used to prepare the clathrate is very expensive. Suzuki et al. do not discuss polyphenolic compounds other than tetrakisphenols.

JP 07 003 191 A, assigned to Kurita, discloses a clathrate of isothiazolones with 5,5'-dichloro-2,2'-dihydroxydiphenylmethane for use in marine antifouling paints. These compositions have achieved limited success because 5,5'-dichloro-2,2'-dihydroxydiphenylmethane is banned in some countries.

There is therefore a continuing need for controlled release biologically active compositions that are inexpensive, compatible in a broad range of loci to be protected, and more effective at controlling the release of the biologically active compound than compositions currently available.

SUMMARY OF THE INVENTION

The present invention is directed to a controlled release composition comprising a biologically active compound and a polyphenolic compound of the formula

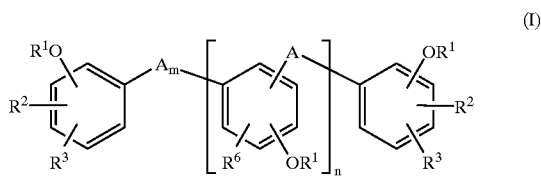

(I)

wherein $A=CR^4R^5$, dicyclopentadiene; $R^1$=H, $(C_1-C_8)$alkyl; $R^2$, $R^3$, $R^4$, $R^5$, $R^6$ are independently selected from $R^1$, $OR^1$, $SR^1$, $NO_2$, CN, $CO_2R^1$, halo, phenyl, substituted phenyl, phenoxy, substituted phenoxy, $(C_1-C_4)$alkoxyphenyl, substituted $(C_1-C_4)$alkoxyphenyl; m=0 or 1; n=0–100; provided that when m=0 n=0; and wherein the polyphenolic compound is optionally crosslinked.

The present invention is also directed to a method of controlling or inhibiting the growth of microorganisms in a locus comprising introducing into or onto the locus to be protected an effective amount of the composition described above.

The present invention is further directed to a method of eliminating or inhibiting the growth of marine organisms on a structure comprising introducing into or onto the structure to be protected an effective amount of the composition described above.

The present invention is further directed to a method of eliminating or inhibiting the growth of fungi, plants and insects comprising introducing into or onto the locus to be protected an effective amount of the composition described above.

DETAILED DESCRIPTION OF THE INVENTION

As used throughout the specification, the following terms shall have the following meanings, unless the context clearly indicates otherwise.

The term "biologically active compounds" refers to microbicides, marine antifouling agents, and agricultural pesticides. "Microbicide" refers to a compound capable of inhibiting the growth of or controlling the growth of microorganisms at a locus. The term "microorganism" includes, but is not limited to, fungi, bacteria, and algae.

"Marine antifouling agent" includes algaecides and molluscicides. "Marine antifouling activity" is intended to include both the elimination of and inhibition of growth of marine organisms. Marine organisms controlled by marine antifouling agents suitable for use in this invention include both hard and soft fouling organisms. Generally speaking, the term "soft fouling organisms" refers to plants and invertebrates, such as slime, algae, kelp, soft corals, tunicates, hydroids, sponges, and anemones, while the term "hard fouling organisms" refers to invertebrates having some type of hard outer shell, such as barnacles, tubeworms, and molluscs.

"Agricultural pesticides" include agricultural fungicides, herbicides and insecticides. "Agricultural fungicide" refers to a compound capable of inhibiting the growth of or controlling the growth of fungi in an agricultural application, such as treatment of plants and soil; "herbicide" refers to a compound capable of inhibiting the growth of or controlling the growth of certain plants; and "insecticide" refers to a compound capable of controlling insects.

"Alkyl" means straight chain, branched, cyclic, or any combination thereof; "halogen" and "halo" mean fluorine, chlorine, bromine, or iodine. "Substituted phenyl," "substituted phenoxy" and "substituted $(C_1-C_4)$alkoxyphenyl" mean one or more of the hydrogens on the aromatic ring are replaced by another substituent, such as cyano, hydroxy, ($C_1$–C4)alkyl, nitro, mercapto, ($C_1$–$C_4$)alkylthio, halo and ($C_1$–C4)alkoxy. All amounts are percent by weight ("%wt"), unless otherwise noted and all %wt ranges are inclusive. As used throughout the specification, the following abbreviations are applied: g=gram; mg=microgram; mL=milliliter; MW=molecular weight; IR=infrared; rpm=revolutions per minute; HPLC=high performance liquid chromatography; ppm=parts per million; and AWPA=American Wood Preservers Association.

The biologically active compounds useful in this invention are those which are hydrogen bond acceptors. That is, the compounds are those having one or more atoms selected from nitrogen, oxygen, fluorine or mixtures thereof. The nitrogen or oxygen may have single or multiple bonds, such as in a carbonyl, imine, nitrile, hydroxy, amide, alkoxy, ester, ether or amine group.

Suitable microbicides of the present invention include, but are not limited to: 5-chloro-2-methyl-3-isothiazolone; 2-methyl-3-isothiazolone; 2-n-octyl-3-isothiazolone; 4,5-dichloro-2-n-octyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; tetrachloroisophthalonitrile; 5-bromo-5-nitro-1,3-dioxane; 2-bromo-2-nitropropanediol; 2,2-dibromo-3-nitrilopropionamide; N,N'-dimethylhydroxyl-5, 5'- dimethylhydantoin; bromochlorodimethylhydantoin; 1,2-benzisothiazolin-3-one; 4,5-trimethylene-2-methyl-3-isothiazolone; 5-chloro-2-(2,4-dichlorophenoxy)phenol and 3,4,4'-trichlorocarbanilide.

Suitable marine antifouling agents of the present invention include, but are not limited to: manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to, 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

Suitable agricultural fungicides of the present invention include, but are not limited to: dithiocarbamate and derivatives such as ferbam, ziram, maneb, mancozeb, zineb, propineb, metham, thiram, the complex of zineb and polyethylene thiuram disulfide, dazomet, and mixtures of these with copper salts; nitrophenol derivatives such as dinocap, binapacryl, and 2-sec-butyl-4,6-dinitrophenyl isopropyl carbonate; heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; miscellaneous halogenated fungicides such as: chloranil, dichlone, chloroneb, tricamba, dichloran, and polychloronitrobenzenes; fungicidal antibiotics such as: griseofulvin, kasugamycin and streptomycin; miscellaneous fungicides such as: diphenyl sulfone, dodine, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy) pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; and pyrimethanil.

Suitable herbicides of the present invention include, but are not limited to: carboxylic acid derivatives, including benzoic acids and their salts; phenoxy and phenyl substituted carboxylic acids and their salts; and trichloroacetic acid and its salts; carbamic acid derivatives, including ethyl N,N-di(n-propyl)thiolcarbamate and pronamide; substituted ureas, substituted triazines, diphenyl ether derivatives such as oxyfluorfen and fluoroglycofen, anilides such as propanil, oxyphenoxy herbicides, uracils, nitriles, and other organic herbicides such as dithiopy and, thiazopyr.

Suitable insecticides of the present invention include, but are not limited to: acephate; aldicarb; alpha-cypermethrin; azinphos-methyl; bifenthrin; binapacryl; buprofezin; carbaryl; carbofuran; cartap; chlorpyrifos; chlorpyrifos methyl; clofentezine; cyfluthrin; cyhexatin; cypermethrin; cyphenothrin; deltamethrin; demeton; demeton-S-methyl; demeton-O-methyl; demeton-S; demeton-S-methyl sulfoxid; demephion-O; demephion-S; dialifor; diazinon; dicofol; dicrotophos; diflubenzuron; dimethoate; dinocap; endosulfan; endothion; esfenvalerate; ethiofencarb; ethion; ethoatemethyl; ethoprop; etrimfos; fenamiphos; fenazaflor; fenbutatin-oxide; fenitrothion; fenoxycarb; fensulfothion; fenthion; fenvalerate; flucycloxuron; flufenoxuron; fluvalinate; fonofos; fosmethilan; furathiocarb; hexythiazox; isazophos; isofenphos; isoxathion; methamidophos; methidathion; methiocarb; methomyl; methyl parathion; mevinphos; mexacarbate; monocrotophos; nicotine; omethoate; oxamyl; parathion; permethrin; phorate; phosalone; phosmet; phosphamidon; pirimicarb; pirimiphosethyl; profenofos; promecarb; propargite; pyridaben; resmethrin; rotenone; tebufenozide; temephos; TEPP; terbufos; thiodicarb; tolclofos-methyl; triazamate; triazophos and vamidothion.

The biologically active compound is preferably a microbicide or a marine antifouling agent. Especially preferred are 2-methyl-3-isothiazolone, 5-chloro-2-methyl-3-isothiazolone, 2-n-octyl-3-isothiazolone, 4,5-dichloro-2-n-octyl-3-isothiazolone, benzisothiazolone, 4,5-trimethylene-3-isothiazolone, 3-iodo-2 -propynyl butyl carbamate; 5-chloro-2-(2,4-dichlorophenoxy)phenol and 3,4,4'-trichlorocarbanilide.

The polyphenolic compounds useful in this invention include, but are not limited to: 2,6-bis(2',4'-dihydroxybenzyl)-4-methylphenol; 4,4'-biphenol; dicyclopentadiene-phenol resins; phenol-formaldehyde condensates; crosslinked phenol-formaldehyde condensates; cresol-formaldehyde condensates, such as 2,6-bis[(2-hydroxy-5-methylphenyl)methyl]-4-methylphenol; and crosslinked cresol-formaldehyde condensates. The phenol-formaldehyde condensates typically have a MW of from 600 to 8000. The cresol-formaldehyde condensates typically have a MW of from 450 to 20,000. The cresol-formaldehyde condensates may be prepared from ortho-, meta-, or para-cresols or mixtures thereof. When crosslinked, the polyphenolic compounds useful in this invention are linked with a methylene bridge.

The polyphenolic compounds useful in this invention are well known in the photoresist and ion exchange fields and are generally commercially available. For example, the phenol-formaldehyde condensates are available as phenol Novolac® resins; the cresol-formaldehyde condensates as cresol Novolac® resins; and the dicyclopentadiene-phenol resins as Durite® resins, all from Borden Chemical, Inc. (Louisville, Ky.). Crosslinked phenol-formaldehyde condensates are available as Duolite® XAD resins from the Rohm and Haas Company (Philadelphia, Pa.).

The compositions of the present invention can be prepared by mixing a solution of the biologically active compound with a solution of the polyphenolic compound. In the alternative, either the biologically active compound or the polyphenolic compound may be added neat to a solution of the other component. For example, a polyphenolic compound may be added neat to a solution of the biologically active compound. The solvent can be removed by any means, such as under reduced pressure, to yield a solid or oily composition. The solvent used to dissolve the biologically active compound may be the same or different from that used to dissolve the polyphenolic compound. When different solvents are used to dissolve the biologically active compound and the polyphenolic compound, it is preferred that they be miscible with each other. Mixtures of solvents may also be used. Suitable solvents include alcohols, such as methanol, ethanol, and propanol; esters, such as ethyl acetate and butyl acetate; ketones, such as acetone and methyl iso-butyl ketone; nitrites, such as acetonitrile; and the like. In the alternative, either the biologically active compound or the polyphenolic compound or both may be blended as a melt. The compositions of the present invention are either solids or oils.

The polyphenolic compounds of the present invention may be loaded with generally from 0.1 %wt to 95%wt of the biologically active compound, based on the weight of the polyphenolic compound. Thus, the weight ratio of biologically active compound to polyphenolic compound in the compositions is generally from 0.1:99.9 to 95:5. Preferably, the weight ratio is from 1:10 to 9:1 and more preferably from 3:10 to 6:1 0.

More than one biologically active compound may be used in the compositions of the present invention as long as the compounds do not react with, or otherwise destabilize, each other and are compatible with the polyphenolic compound. This has the advantage of controlling the release of multiple biologically active compounds which may provide a broader spectrum of control than one compound alone. Also, this may reduce the cost of treatment when multiple biologically active compounds must be used. When more than one biologically active compound is used, the ratio of the total amount of the biologically active compounds to the polyphenolic compound is generally from 0.1:99.9 to 95:5.

The compositions of the invention may further comprise a carrier, such as water, organic solvent or mixtures thereof. Suitable organic solvent carriers include, but are not limited to: acetonitrile, ethyl acetate, butyl acetate, toluene, xylene, methanol, ethanol, acetone, methyl ethyl ketone, methyl isobutyl ketone, ethylene glycol, diethylene glycol, propylene glycol, dipropylene glycol, and glycol ethers. When the compositions of the invention are to be used in an agricultural application, it is preferred that the carrier be an agronomically acceptable carrier.

The compositions of the invention are useful wherever the biologically active compound would be useful. When the biologically active compound is a microbicide, the compositions of the invention are useful in controlling or inhibiting the growth of microorganisms, such as bacteria and fungi, in a locus. The compositions of the invention are suitable for use in any locus requiring protection from microorganisms. Suitable loci include, but are not limited to: cooling towers; air washers; mineral slurries; pulp and paper processing fluids; paper coatings; swimming pools; spas; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood, including lumber, timber, fiberboard, plywood, and wood composites; plastics; lubricants; hydraulic fluids; medical devices; metalworking fluids; emulsions and dispersions; paints, including marine paints; varnishes, including marine varnishes; latexes; odor control fluids; coatings, including marine coatings; petroleum processing fluids; fuel; oil field fluids; photographic chemicals; printing fluids; sanitizers; detergents; textiles; and textile products.

When compositions of the invention comprise a microbicide, they can either be added directly to the locus to be protected or added as a composition further comprising a suitable carrier. Suitable carriers useful for microbicidal applications include, but are not limited to, water; organic solvent, such as ethylene glycol, diethylene glycol, propylene glycol, dipropylene glycol, xylene, toluene, acetone, methyl iso-butyl ketone, or esters; or mixtures thereof. The compositions may also be formulated as microemulsions, microemulsifiable concentrates, emulsions, emulsifiable concentrates, pastes, or may be encapsulated. The particular formulation will depend upon the locus to be protected and the particular microbicide used. The preparation of these formulations is by well known, standard methods.

When the compositions comprise a microbicide, the amount of the compositions of the invention necessary to control or inhibit the growth of microorganisms depends upon the locus to be protected, but is typically sufficient if it provides from 0.5 to 2500 ppm of microbicide, at the locus to be protected. Microbicides are often used in loci that require further dilution. For example, the compositions of the invention may be added to a metal working fluid concentrate, which is then further diluted. The amount of the compositions of the invention necessary to control microorganism growth in the final metal working fluid dilution are sufficient if they provide generally from 5 to 50 ppm of the microbicide in the final dilution. In loci such as a paint, which is not further diluted, the amount of the compositions of the invention necessary to control microorganism growth are sufficient if they provide generally from 500 to 2500 ppm of the microbicideu.

When the biologically active compound of the present invention is a marine antifouling agent, the compositions of the present invention can be used to inhibit the growth of marine organisms by application of the compositions onto or into a marine structure. Depending upon the particular marine structure to be protected, the compositions of the present invention can be directly incorporated into the marine structure, applied directly to the marine structure, or incorporated into a coating which is then applied to the marine structure.

Suitable marine structures include, but are not limited to: boats, ships, oil platforms, piers, pilings, docks, elastomeric rubbers, and fish nets. The compositions of the present invention are typically directly incorporated into structures such as elastomeric rubber or fish net fibers during manufacture. Direct application of the compositions of the invention is typically made to structures such as fish nets or wood pilings. The compositions of the invention can also be incorporated into a marine coating, such as a marine paint or varnish.

When the compositions of the invention comprise a marine antifouling agent, the amount of the compositions of the invention necessary to inhibit or prevent the growth of marine organisms is typically sufficient if it provides from 0.1 to 30% wt of marine antifouling agent alone, based on the weight of the structure to be protected or based on the weight of the coating to be applied. When the compositions of the invention are directly incorporated into or directly applied onto a structure, the amount of the compositions necessary to inhibit the growth of marine organisms is generally sufficient if it provides 0.1 to 30% wt of marine antifouling agent alone, based on the weight of the structure. It is preferred that the amount of the compositions of the invention be sufficient to provide 0.5 to 20% wt of marine antifouling agent alone; more preferably, 1 to 15% wt. When incorporated into a coating, the amount of the compositions of the invention suitable to inhibit the growth of marine organisms is generally sufficient if it provides 0.1 to 30% wt of marine antifouling agent alone, based on the weight of said coating. The amount of the compositions of the invention preferably provides 0.5 to 15% wt of marine antifouling agent alone; more preferably, 1 to 10% wt.

In general, the compositions of the invention comprising a marine antifouling agent are incorporated in a carrier such as water; organic solvent, such as xylene, methyl isobutyl ketone, and methyl isoamyl ketone; or mixtures thereof.

Direct applications of the compositions of the invention may be by any conventional means, such as dipping, spraying, or coating. Fish nets, for example, may be also protected by dipping the fish nets into a composition comprising the compositions of the invention and a carrier or by spraying the fish nets with said composition.

Structures such as wood pilings and fish nets may be protected by directly incorporating the compositions of the invention into the structure. For example, a composition of the invention further comprising a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The compositions of the invention are suitable for use in both solvent- and water-based marine coatings. Solvent-based marine coatings are preferred.

Any conventional binder may be utilized in the marine antifouling coating incorporating the compositions of the invention. Suitable binders include, but are not limited to: polyvinyl chloride in a solvent-based system; chlorinated rubber in a solvent based system; acrylic resins in solvent-based or aqueous systems; vinyl chloride-vinyl acetate copolymer systems as aqueous dispersions or solvent-based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and controlled release materials, such as rosin. Water-based coatings may also optionally contain: coalescents, dispersants, surface active agents, rheology modifiers, or adhesion promoters. Solvent-based coatings may also optionally contain extenders, plasticizers, or rheology modifiers.

A typical marine coating comprises 2 to 20% wt binders, up to 15% wt rosins/modified rosins, 0.5 to 5% wt plasticizers, 0.1 to 2% wt antisettling agent, 5 to 60% wt solvent/diluent, up to 70% wt cuprous oxide, up to 30%wt pigments (other than cuprous oxide), and up to 15% wt marine antifouling agent.

Marine coatings containing the compositions of the invention may be applied to a structure to be protected by any of a number of conventional means. Suitable means of application include, but are not limited to, spraying; rolling; brushing; or dipping.

When the biologically active compound is an agricultural pesticide, the compositions of the invention may be applied to plants or soil or may be used as seed treatments. The compositions may be used directly or formulated as dusts, granules, flowables, emulsifiable concentrates, microemulsifiable concentrates, emulsions, microemulsions, or may be encapsulated.

The following examples are presented to illustrate further various aspects of the present invention, but are not intended to limit the scope of the invention in any aspect.

EXAMPLE 1

The following are examples of compositions of the present invention prepared according to either of the following general methods.

A. Solution Method

A solution of the biologically active compound in methanol was placed in a flask. To this solution was added a solution of the polyphenolic compound in methanol or ethanol. The amount of the biologically active compound used was such that the final product contained from 31–56% wt of the biologically active compound based on the weight of the polyphenolic compound. The methanol or ethanol was then removed in vacuo at 50° C. to yield either a solid or an oil.

B. Melt Method

The biologically active compound was placed in a flask and melted. The melted biologically active compound was added to a solution or suspension of the polyphenolic compound in methanol or ethanol. The amount of the biologically active compound used was such that the final product contained from 13–79% wt of the biologically active compound based on the weight of the polyphenolic compound. The methanol or ethanol was then removed in vacuo at 500 C to yield either a solid or an oil.

The compositions prepared are reported in Table 1 along with the IR frequency of the complexed isothiazolone carbonyl. The amount of biologically active compounds in the compositions are reported as %wt based on the weight of the polyphenolic compound. The abbreviations used in Table 1 are as follows.

Polyphenolic Compound

A1=2,6-bis(2',4'-dihydroxybenzyl)-4-methylphenol

A2=phenol-formaldehyde condensate having MW=2000 (Phenyl Novolac 7SD-1711)

A3=phenol-formaldehyde condensate having MW=1000 (Phenyl Novolac SD-1731A)

A4=phenyl-formaldehyde resin with a hydroxyl functionality of 4 to 5 (Phenyl Novolac SD-3418)

A5=phenol-formaldehyde resin with a hydroxyl functionality of 6 to 7 (Phenyl Novolac SD-838A)

A6=2,6-bis[(2-hydroxy-5-methylphenyl)methyl]-4-methylphenol

A7=crosslinked phenol-formaldehyde condensate (Duolite XAD-761)

Biologically Active Compound

B1=4,5-dichloro-2-n-octyl-3-isothiazolone

B2=3:1 mixture of 5-chloro-2-methyl-3-isothiazolone and 2-methyl-3-isothiazolone B3=2-methyl-3-isothiazolone B4=2-n-octyl-3-isothiazolone B5=3,4,4'-trichlorocarbanilide

TABLE 1

Compositions of the Invention

| Sample | Polyhenolic Compound | Biologically Active Compound (% wt) | Method of Preparation | IR cm$^{-1}$ | Physical State |
|---|---|---|---|---|---|
| 1 | A1 | B1 (43) | A | 1642 | Oil |
| 2 | A2 | B1 (38) | B | 1640 | Oil |
| 3 | A3 | B1 (36) | B | 1642 | Oil |
| 4 | A4 | B1 (39) | B | 1642 | Oil |
| 5 | A5 | B1 (37) | B | 1640 | Oil |
| 6 | A6 | B1 (56) | A | 1639 | Solid |
| 7 | A2 | B2 (30) | A | | Solid |
| 8 | A6 | B2 (31) | A | | Solid |
| 9 | A2 | B3 (40) | B | 1582 | Oil |
| 10 | A2 | B4 (40) | B | 1588 | Oil |
| 11 | A2 | B5 (45) | A | | Solid |
| 12 | A2 | B1 (79) | B | | Oil |
| 13 | A2 | B1 (13) | B | | Oil |
| 14 | A7 | B1 (49) | B | | Solid |
| Control | — | B1 | — | | |

EXAMPLE 2

The compositions of Example 1 were evaluated for their rate of release of the biologically active compound according to the following procedure.

A weighed amount of a sample was placed in a 100 mL sample jar. To the jar was then added 100 mL of water containing 0.2% wt of sodium octylfosuccinate. The solution was then gently stirred to ensure no foam was formed. Aliquots (0.5 mL) were taken at various time points and transferred to a microcentrifuge tube. Each aliquot was then centrifuged at 14,000 rpm for 3 minutes. The supernatant was then removed and analyzed by HPLC for the amount of the biologically active compound. The microcentrifuge tube was then washed with 0.5 mL of water containing 0.2% wt of sodium octylsulfosuccinate and the wash liquid added to the sample jar. This ensured that none of the particles removed during sampling were lost and that the volume in the jar remained constant. The cumulative percentages of 4,5-dichloro-2-n-octyl-3-isothiazolone released are reported in Table 2.

TABLE 2

% of 4,5-Dichloro-2-n-octyl-3-isothiazolone Released

| Time (min) | Sample 1 | Sample 2 | Sample 4 | Sample 5 | Sample 12 | Sample 14 |
|---|---|---|---|---|---|---|
| 2460 | | | | | 2.8 | |
| 2640 | 3.4 | | | | | |
| 3840 | | | | | | 12.2 |
| 4200 | | 1.3 | 0.6 | 1.0 | | |
| 5520 | 5.8 | | | | | |
| 5580 | | | | | 6.2 | |
| 7080 | | 2.1 | 1.1 | 1.5 | | |
| 9840 | 8.4 | | | | | |
| 9960 | | | | | 8.8 | 23.3 |
| 10140 | | 2.8 | 1.5 | 2.0 | | |
| 16800 | | | | | | 33.2 |

The above data clearly show that the compositions of the invention trolled release of 4,5-dichloro-2-n-octyl-3-isothiazolone.

EXAMPLE 3

The compositions of Example 1 were evaluated for control of the release of biologically active compound in wood.

A sufficient amount of Sample 13 (Table 1) was taken up in ethanol to provide a 1300 ppm treatment solution, based on 4,5-dichloro-2-n-octyl-3-isothiazolone. A Control sample was prepared by dissolving 4,5-dichloro-2-n-octyl-3-isothiazolone by itself in ethanol, to yield a 1300 ppm solution. Both samples were used to treat blocks of Southern Yellow Pine according to AWPA Standard M11-87. Eight wood blocks were pressure treated with the Sample 13 treatment solution and eight blocks were treated with the Control treatment solution. Six of each set of blocks were allowed to dry for 3 weeks and then repressurized with water. The blocks were weighed to determine the nominal amount of 4,5-dichloro-2-n-octyl-3-isothiazolone taken up into the blocks. Blocks treated with the Sample 13 treatment solution contained a total 4,5-dichloro-2-n-octyl-3-isothiazolone nominal content of 26,726 µg and blocks treated with the Control treatment solution showed a total 4,5-dichloro-2-n-octyl-3-isothiazolone nominal content of 26,985 µg. Therefore, equivalent amounts of 4,5-dichloro-2-n-octyl-3-isothiazolone were impregnated into the wood blocks. Six blocks of each treatment set were then immersed in water for a period of time. The water was then removed and analyzed by HPLC to determine the amount of 4,5-dichloro-2-n-octyl-3-isothiazolone that had leached from the wood blocks. Fresh water was then added to the wood blocks and the test repeated. These results are reported in Table 3.

TABLE 3

Amount of 4,5-Dichloro-2-n-octyl-3-isothiazolone Leached

| Time (hours) | Sample 13 (ppm) | Control (ppm) |
|---|---|---|
| 4 | 0.51 | 2.19 |
| 22 | 0.58 | 2.24 |
| 72 | 0.59 | 2.27 |
| 164 | 0.55 | 2.03 |
| 218 | 0.53 | 1.91 |
| 267 | 0.48 | 1.61 |
| 339 | 0.47 | 1.63 |
| 386 | 0.44 | 1.47 |
| 506.5 | 0.34 | 1.07 |
| Total ppm Leached | 4.49 | 16.42 |

The above data clearly show that the compositions of the invention greatly reduce the amount of 4,5-dichloro-2-n-octyl-3-isothiazolone leached from the wood (Sample 13) as compared to conventionally treated wood (Control).

What is claimed:

1. A controlled release composition comprising
    (a) at least 0.5 ppm of a biologically active compound selected from the group consisting of: 5-chloro-2-methyl-3-isothiazolone; 2-methyl-3-isothiazolone;

2-n-octyl-3-isothiazolone; 4,5-dichloro-2-n-octyl-3-isothiazolone; 1,2-dibromo-2,4-dicyanobutane; methylene-bis-thiocyanate; 2-thiocyanomethylthiobenzothiazole; tetrachloroisophthalonitrile; 5-bromo-5-nitro-1,3-dioxane; 2-bromo-2-nitropropanediol; 2,2-dibromo-3-nitrilopropionamide; N,N'-dimethylhydroxyl-5,5'-dimethylhydantoin; bromochlorodimethylhydantoin; 1,2-benzisothiazolin-3-one; 4,5-trimethylene-2-methyl-3-iosthiazolone; 5-chloro-2-(2,4-dichlorophenoxy)phenol; 3,4,4'-trichlorocarbanilide; manganese ethylenebisdithiocarbamate; zinc dimethyl dithiocarbamate; 2-methyl-4-t-butylamino-6-cvclopropylamino-s-triazine; 2,4,5,6-tetrachloroisophthalonitrile; N,N-dimethyl dichlorophenyl urea; zinc ethylenebisdithiocarbamate; N-(fluorodichloromethylthio)-phthalimide; N,N-dimethyl-N'-phenyl-N'-fluorodichloromethylthiosulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; bis dimethyl dithiocarbamoyl zinc ethylenebisdithiocarbamate; phenyl (bispyridil) bismuth dichloride; 2-(4-thiazolyl)-benzimidazole; pyridine triphenyl borane; phenylamides; halopropargyl compounds; and 2-haloalkoxyaryl-3-isothiazolones;

(b) a polyphenolic compound of the formula

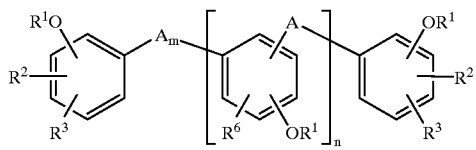

(I)

wherein:
A=CR⁴R⁵, dicyclopentadiene;
R¹=H, (C₁–C₈)alkyl;
R², R³, R⁴, R₅, R⁶ are independently selected from R¹, OR¹, SR¹, NO₂, CN, CO₂R¹, halo, phenyl, substituted phenyl, phenoxy, substituted phenoxy, (C₁–C₄) alkoxyphenyl, substituted (C₁–C₄)alkoxyphenyl;
m=1;
n=1–100; and (c) an organic solvent carrier;
wherein the biologically active compound and the polyphenolic compound are in a weight ratio relative to each other of from 1:10 to 9:1; and wherein the polyphenolic compound is optionally crosslinked.

2. A coating composition comprising from 0.1 to 30 weight percent, based on weight of the coating, of the controlled release composition of claim 1.

3. The composition of claim 1 wherein the biologically active compound is selected from the group consisting of 2-methyl-3-isothiazolone, 5-chloro-2-methyl-3-isothiazolone, 2-n-octyl-3-isothiazolone, 4,5-dichloro-2-n-octyl-3-isothiazolone, benzisothiazolone, 4,5-trimethylene-3-isothiazolone, 3-iodo-2-propynyl butyl carbamate; 5-chloro-2-(2,4-dichlorophenoxy)phenol and 3,4,4'-trichlorocarbanilide.

4. The composition of claim 1 wherein the polyphenolic compound is selected from the group consisting of 2,6-bis (2',4'-dihydroxybenzyl)-4-methylphenol; dicyclopentadiene-phenol resins; phenol-formaldehyde condensates; crosslinked phenol-formaldehyde condensates; cresol-formaldehyde condensates; and crosslinked cresol-formaldehyde condensates.

5. The coating composition of claim 2 wherein the composition is a marine coating composition further comprising a binder and a solvent.

6. The coating composition of claim 5 wherein the binder is selected from one or more of polyvinyl chloride in a solvent-based system, chlorinated rubber in a solvent-based system, acrylic resins in solvent based systems, vinyl chloride-vinyl acetate copolymer in solvent-based systems, butadiene-styrene rubbers, butadiene-acrylonitrile rubbers, butadiene-styrene-acrylonitrile rubbers, drying oils, asphalt, epoxies and siloxanes.

7. The composition of claim 1 further comprising a carrier is selected from the group consisting of acetonitrile, ethyl acetate, butyl acetate, toluene, xylene, methanol, ethanol, acetone, methyl ethyl ketone, methyl iso-butyl ketone, ethylene glycol, diethylene glycol, propylene glycol, and dipropylene glycol.

8. A method for controlling or inhibiting the growth of fungi, bacteria, algae, marine fouling organisms, plants, and insects comprising introducing a composition of claim 1 to a locus to be protected.

9. The method of claim 8 wherein the locus to be protected is selected from: cooling towers; air washers; mineral slurries; pulp and paper processing fluids; paper coatings; adhesives; caulks; mastics; sealants; agriculture adjuvant preservation; construction products; cosmetics and toiletries; shampoos; disinfectants and antiseptics; formulated industrial and consumer products; soaps; laundry rinse waters; leather and leather products; wood; plastics; lubricants; hydraulic fluids; medical devices; metalworking fluids; emulsions and dispersions; paints; varnishes; latexes; odor control fluids; coatings; petroleum processing fluids; fuel; oil field fluids; photographic chemicals; printing fluids; sanitizers; detergents; textiles; textile products; marine structures; plants; soil; and seeds.

10. The method of claim 9 wherein the marine structure is selected from the group consisting of boats, ships, oil platforms, piers, pilings, docks, elastomeric rubbers, and fish nets.

11. The composition of claim 1 wherein the polyphenolic compound is a phenol-formaldehyde condensate and the biologically active compound is 4,5-dichloro-2-n-octyl-3-isothiazolone.

12. A method for controlling or inhibiting the growth of marine fouling organisms comprising introducing a composition of claim 11 to a marine structure.

13. The composition of claim 1 comprising more than one biologically active compound.

14. The coating composition of claim 2 wherein the polyphenolic compound is selected from one or more of phenol-formaldehyde condensates and cresol-formaldehyde condensates.

* * * * *

UNITED STATES PATENT AND TRADEMARK OFFICE
CERTIFICATE OF CORRECTION

PATENT NO. : 6,221,374 B1
DATED : April 24, 2001
INVENTOR(S) : Tirthankar Ghosh & Edwin H. Nungesser It is certified that error appears in the above-identified patent and that said Letters Patent is hereby corrected as shown below:

Column 8,
Line 38, "500 C" should read -- 50° C --;
Line 49, "7SD-1711" should read -- SD-1711 --;
Line 52, "phenyl" should read -- phenol --.

Column 9,
Line 62, "trolled" should read -- provide controlled --.

Signed and Sealed this

Second Day of October, 2001

Attest:

NICHOLAS P. GODICI
*Attesting Officer*     *Acting Director of the United States Patent and Trademark Office*